(12) United States Patent
Vaidya

(10) Patent No.: US 9,517,137 B2
(45) Date of Patent: Dec. 13, 2016

(54) MINIMALLY INVASIVE INTERNAL ELBOW FIXATION HINGE APPARATUS AND SURGICAL METHOD OF APPLYING SAID DEVICE

(71) Applicant: Rahul Vaidya, Ann Arbor, MI (US)

(72) Inventor: Rahul Vaidya, Ann Arbor, MI (US)

( * ) Notice: Subject to any disclaimer, the term of this patent is extended or adjusted under 35 U.S.C. 154(b) by 106 days.

(21) Appl. No.: 14/690,468

(22) Filed: Apr. 19, 2015

(65) Prior Publication Data

US 2016/0302932 A1    Oct. 20, 2016

(51) Int. Cl.
*A61F 2/38*    (2006.01)

(52) U.S. Cl.
CPC ...... *A61F 2/3804* (2013.01); *A61F 2002/3813* (2013.01)

(58) Field of Classification Search
CPC .................... A61F 2/3804; A61F 2002/3813
See application file for complete search history.

(56) References Cited

U.S. PATENT DOCUMENTS

2014/0121779 A1*  5/2014  Gonzalez-Hernandez  A61F 2/30
                                                623/20.12

* cited by examiner

*Primary Examiner* — Jason-Dennis Stewart
(74) *Attorney, Agent, or Firm* — David W. Schumaker

(57) ABSTRACT

A surgical method and internal elbow hinge apparatus for minimally invasive treatment of an unstable elbow (with or without humeral/ulnar bone fractures). The method includes surgically installing the internal elbow hinge which includes a humeral plate, an ulnar plate, and a hinge arm pivotally connected to the humeral plate and fixedly connected to the ulnar plate.

20 Claims, 18 Drawing Sheets

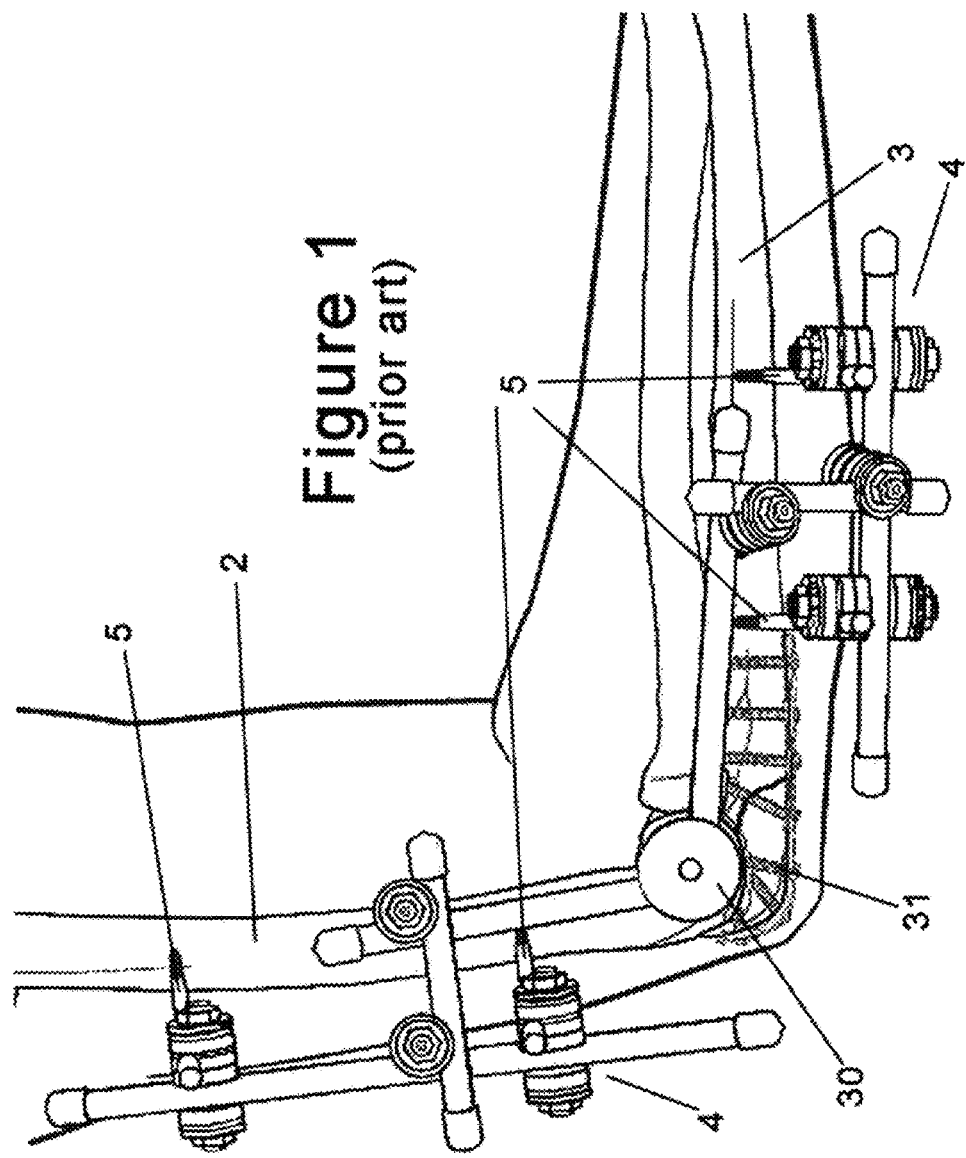

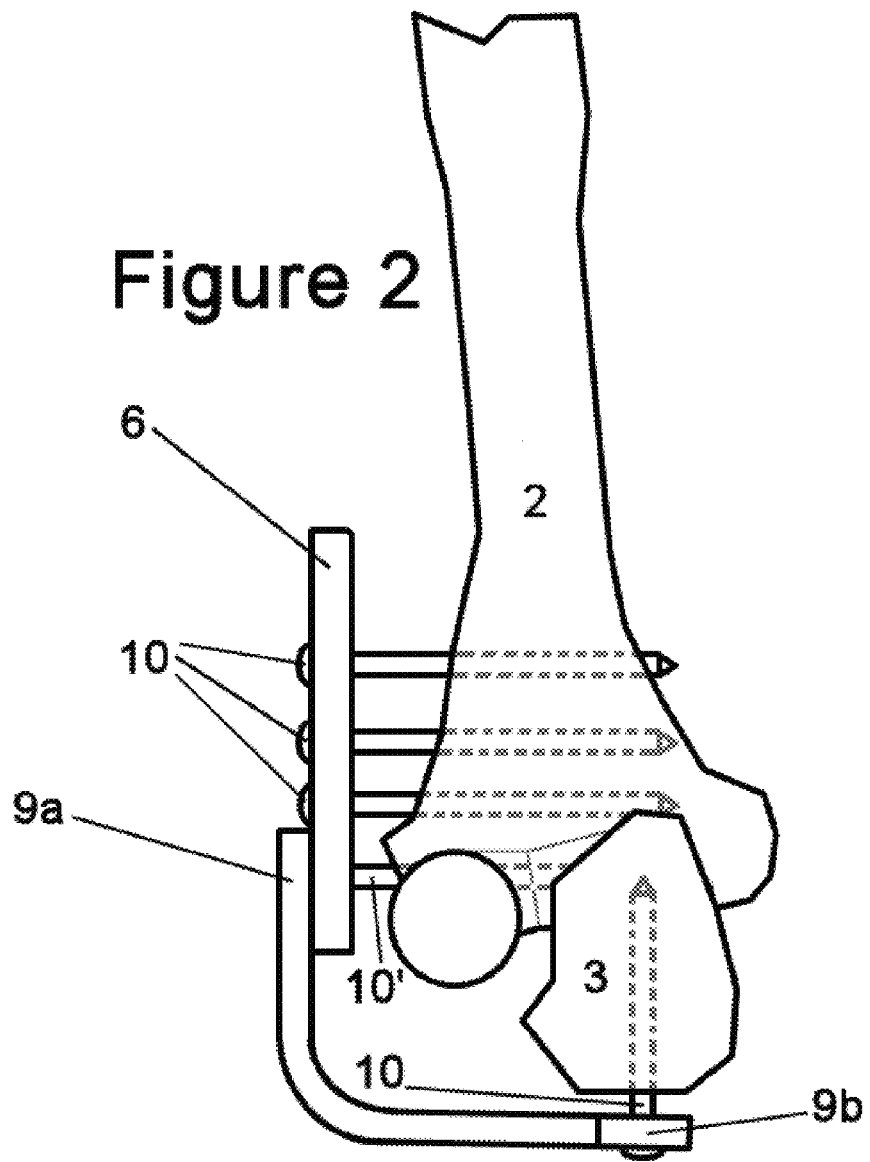

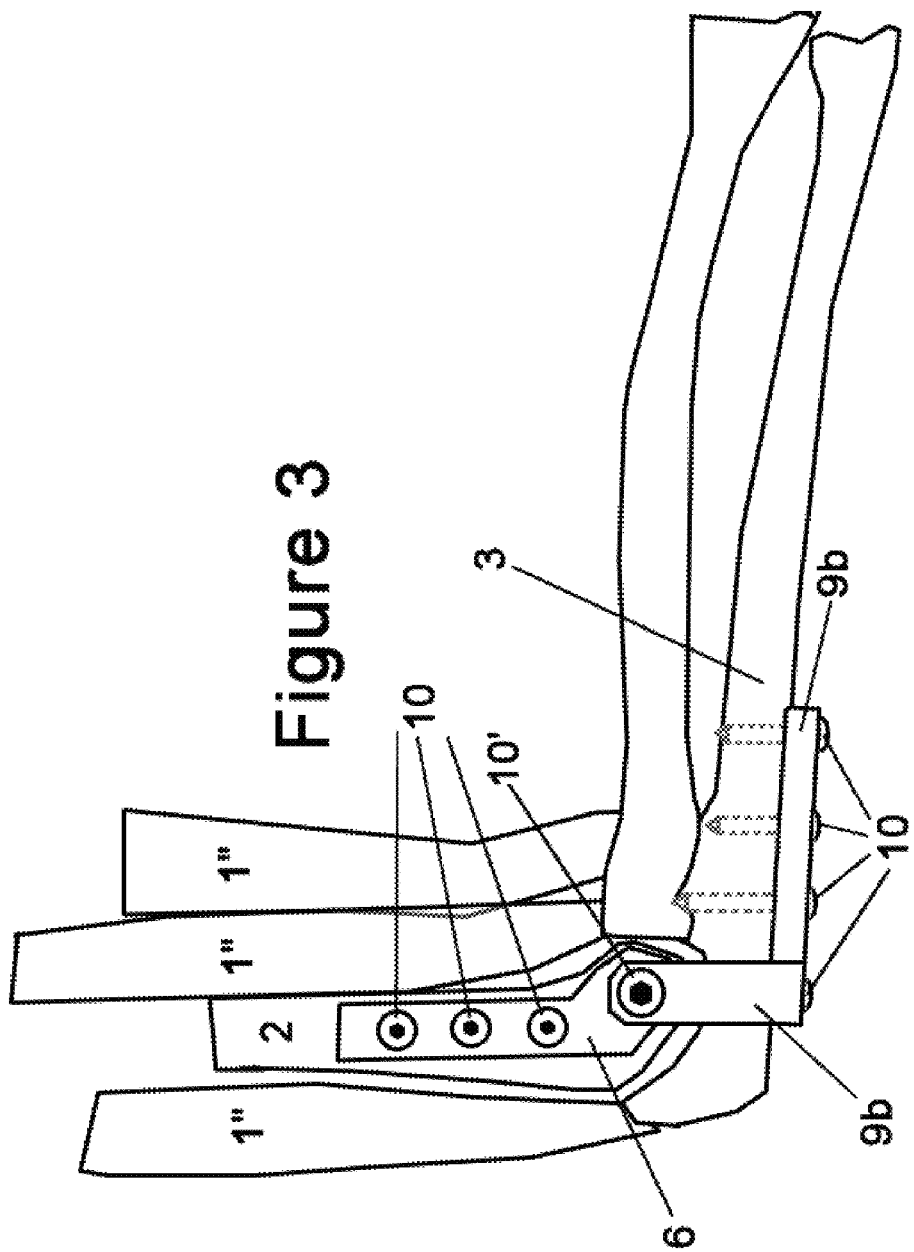

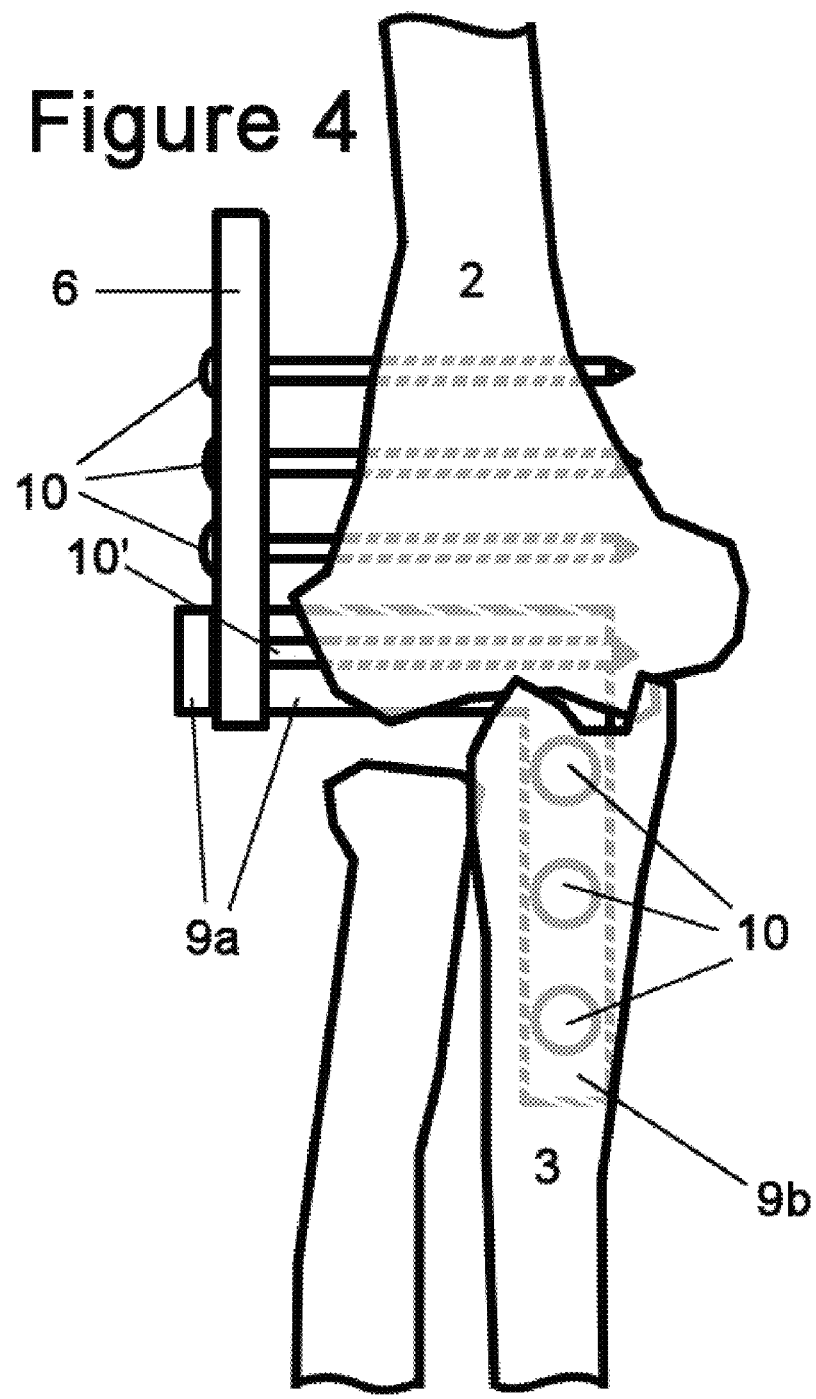

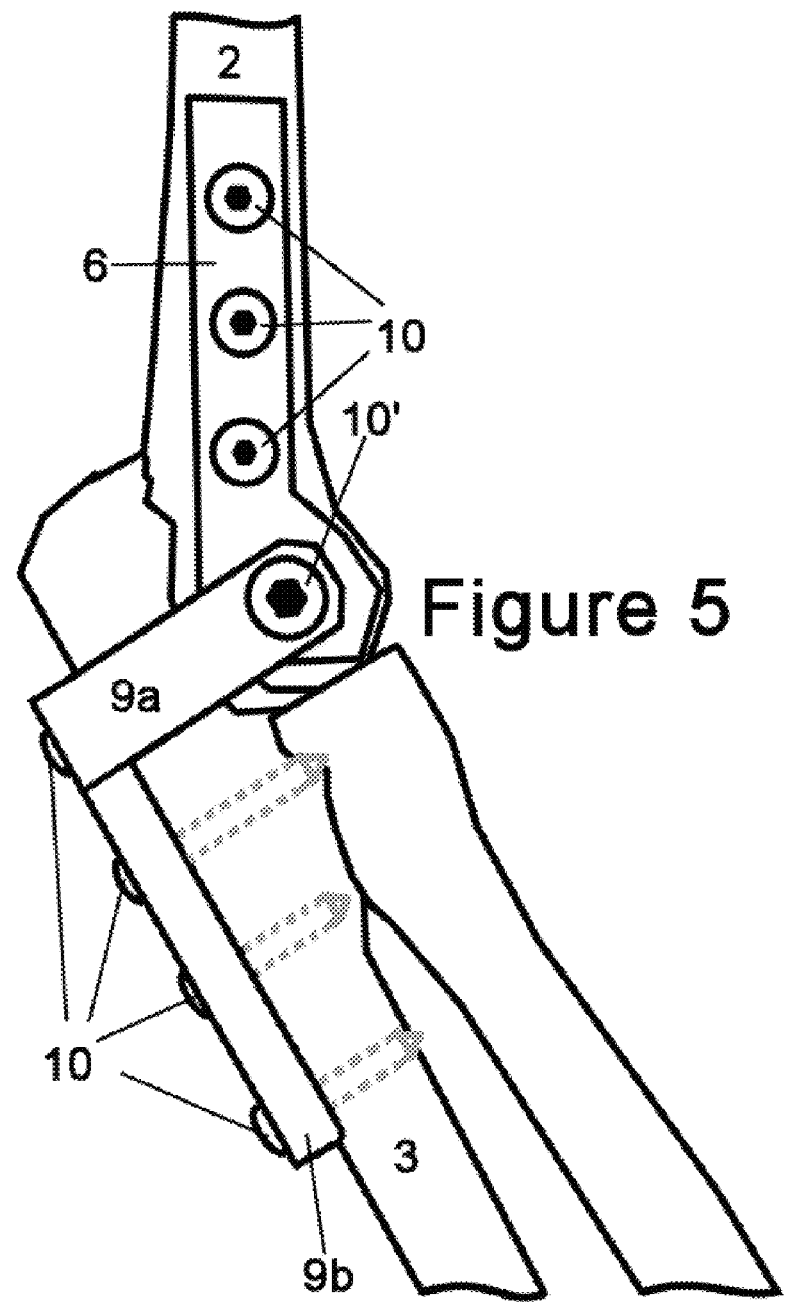

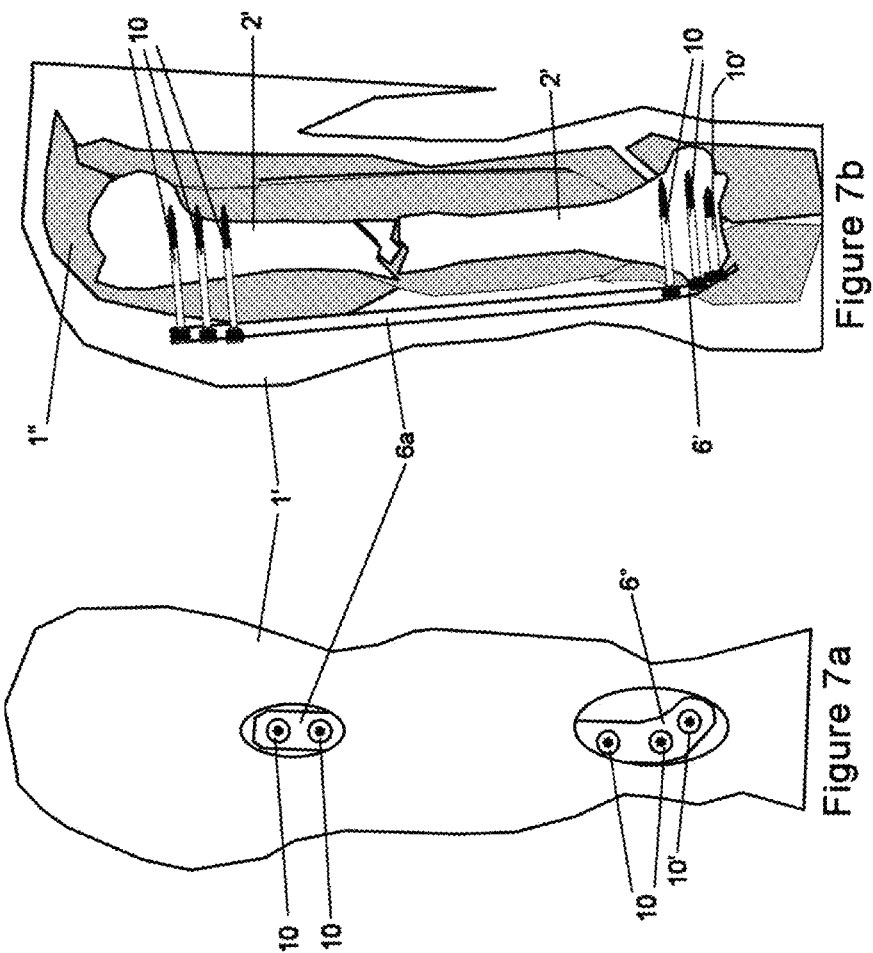

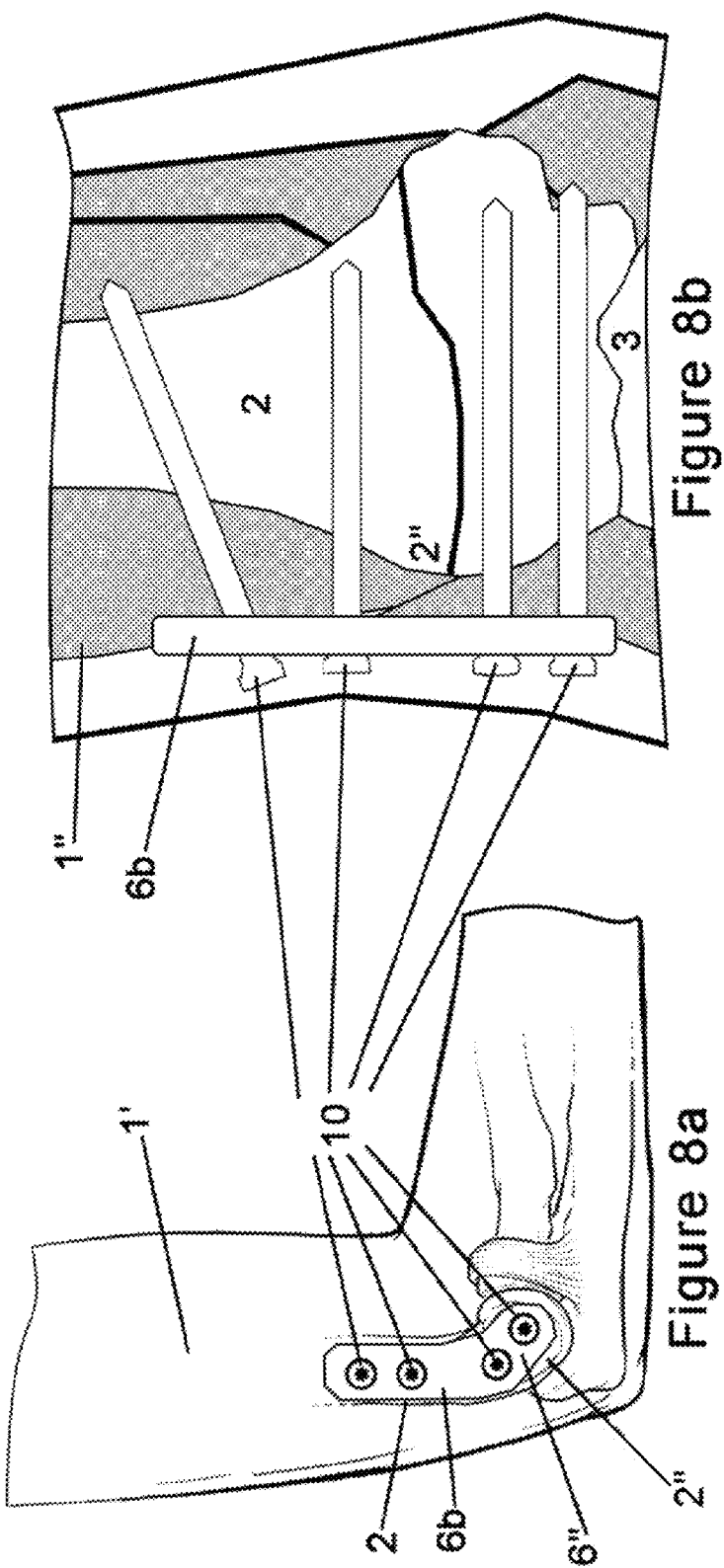

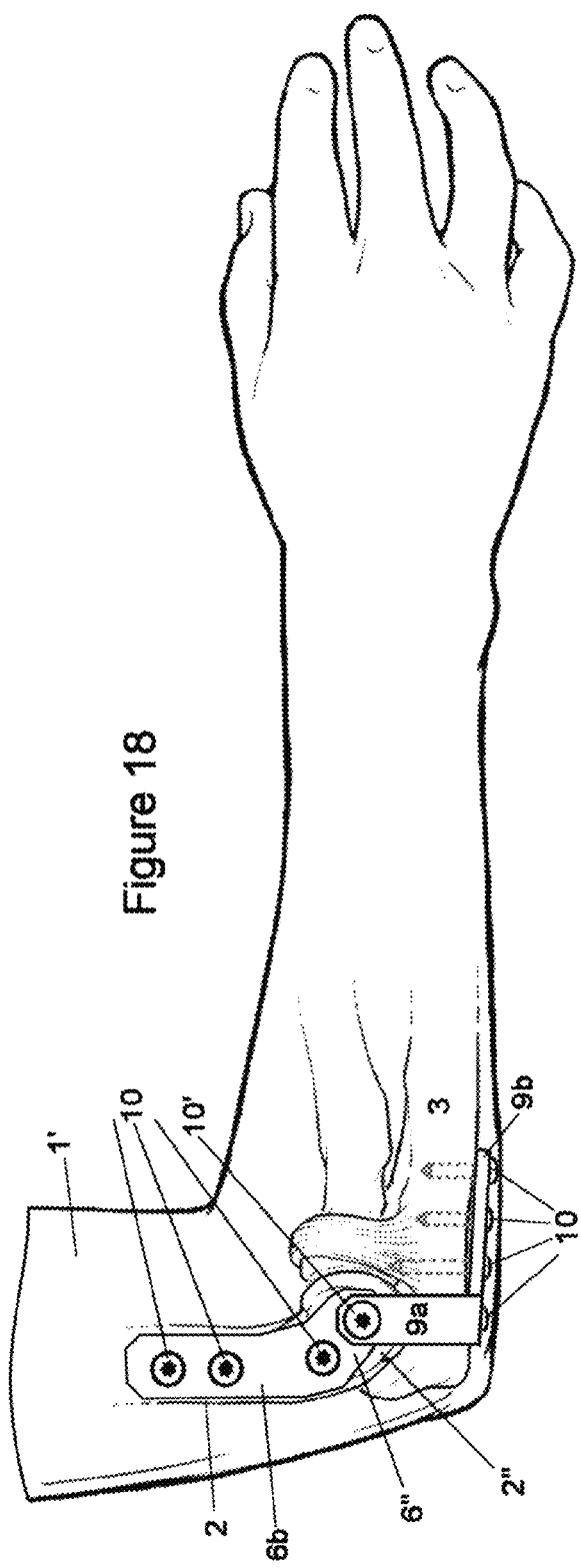

MINIMALLY INVASIVE INTERNAL ELBOW FIXATION HINGE APPARATUS AND SURGICAL METHOD OF APPLYING SAID DEVICE

FIELD OF THE INVENTION

The present invention relates generally to orthopedic implants and minimally invasive methods for insertion thereof. Specifically the present invention relates to an orthopaedic implant elbow hinge and surgical method for minimally invasive insertion thereof.

BACKGROUND OF THE INVENTION

In certain orthopedic surgical procedures, it is necessary to employ an external fixation device for immobilizing or restricting motion of a hinged joint such as the elbow joint. Current external fixation technology includes two main groups of devices: static fixation systems and hinged fixation systems.

Static external fixation has been used in the upper limb for decades, including the elbow. A drawback with static external fixation is that the joint becomes stiff without motion. The fixator systems for static application can also be difficult to dismantle and reassemble for post-operative mobilization. Therefore, once applied, these static fixation systems can lead to more stiffness and suboptimal results.

Existing hinged devices include a single joint axis that can be unlocked so that the arm can be flexed and extended while the external fixator remains connected to the humerus and ulna. These external hinged devices are challenging to apply and, unless used on a frequent basis, can require long operative time. Furthermore, they leave pins protruding through the skin increasing the potential for pin site sepsis or colonization. Furthermore, the external hinged devices are bulky making it difficult for the patient to be comfortable and perform ordinary daily tasks without the device getting in the way due to the excessive size and weight of the external elbow joint fixators.

Thus there is a need in the art for a novel method and construct for minimally invasive treatment/fixation of an unstable elbow joint (with or without bone fractures) using an internal elbow hinge system.

SUMMARY OF THE INVENTION

The present invention comprises a surgical method and internal elbow hinge apparatus for minimally invasive treatment of an unstable elbow (with or without humeral/ulnar bone fractures). The method includes surgically installing the internal elbow hinge which includes a humeral plate, an ulnar plate, and a hinge arm pivotally connected to the humeral plate and fixedly connected to the ulnar plate. The method of installing the internal elbow hinge may include the steps of: tunneling the humeral plate subcutaneously and supramuscularly in the subcutaneous fat layer adjacent the humerus, the length dimension of the humeral plate being generally substantially parallel to the length dimension of the humerus; attaching the humeral plate to the humerus, the humeral plate spanning at least the distal region of the humerus, wherein the humeral plate remains disposed in the subcutaneous fat layer and away from, but substantially parallel to the humerus once attached to the humerus; tunneling the hinge arm subcutaneously and supramuscularly in the subcutaneous fat layer between the posterior proximal ulna region and the distal end of the humeral plate through the lateral circumference of the proximal forearm; pivotally attaching the hinge arm to the distal end of the humeral plate; tunneling the ulnar plate subcutaneously and supramuscularly in the subcutaneous fat layer from the posterior proximal ulna toward the distal end of the ulna, the length dimension of the ulnar plate being generally substantially parallel to the length dimension of the ulna; attaching the ulnar plate to the ulna, the ulnar plate spanning at least the proximal region of the ulna, wherein the ulnar plate remains disposed in the subcutaneous fat layer and away from, but substantially parallel to the ulna once attached to the ulna; and attaching the end of the hinge arm adjacent to the ulnar plate to the proximal end of the ulnar plate.

The method may further include attaching the humeral plate to the humerus by inserting attachment screws through holes in the humeral plate and into the humerus; and attaching the ulnar plate to the ulna includes attaching the ulnar plate to the ulna by inserting attachment screws through holes in the ulnar plate and into the ulna. The humeral and ulnar plates may be threaded and the attachment screws may have threaded heads. The threaded heads may allow the attachment screws to lock into the threaded holes of the humeral and ulnar plates. The humeral plate may have an angled and/or contoured distal end to anatomically match the lateral epicondyle region of the distal end of the humerus.

The humeral plate may be an elongated humeral plate that spans substantially the length of the humerus and the tunneling step includes creating one or more incisions in the skin on the lateral part of the brachium through which the elongated humeral plate can be inserted into the subcutaneous fat layer. The step of attaching the humeral plate to the humerus may further include inserting attachment means through holes in the proximal end of the elongated humeral plate and the step distracting and aligning a humerus having a fracture of the humeral shaft. The step of distracting and aligning the humerus having a fracture of the humeral shaft may include inserting a threaded rod into the proximal end of the humerus having a fracture of the humeral shaft and manually distracting and aligning the humerus having a fracture of the humeral shaft. Alternatively, the step of distracting and aligning the humerus having a fracture of the humeral shaft may include using a distraction device.

The step of using a distraction device may include the step of attaching the distraction device to holes in the proximal end of elongated humeral plate and also attaching the distraction device to the proximal end of the humerus having a fracture of the humeral shaft. The distraction device may have two brackets, where the first of the brackets is attached to the holes in the proximal end of the elongated humeral plate and the second of the brackets is attached to the proximal end of the humerus having a fracture of the humeral shaft. The distraction device may further includes an expansion device which is attached to both brackets and includes a threaded rod and a nut which is threaded onto the threaded rod, wherein the nut pushes against one of the brackets causing the brackets to expand away from each other thereby providing for distraction of the humerus having a fracture of the humeral shaft.

The step of attaching the humeral plate to the humerus may further include the step of inserting an attachment screw through a hole in a proximal end of the elongated humeral plate into the proximal end of the humerus having a fracture of the humeral shaft once the step of distracting and aligning the humerus having a fracture of the humeral shaft is completed; and the step of removing the distraction device after the step of inserting an attachment screw through a hole in the proximal end of the elongated humeral plate into the proximal end of the humerus having a fracture of the humeral shaft. The step of attaching the humeral plate to the humerus may further include the step of inserting an additional attachment screw through each of the remaining holes in the proximal end of the elongated plate into the proximal end of the humerus.

The step of tunneling the hinge arm subcutaneously and supramuscularly in the subcutaneous fat layer between the posterior proximal ulna region and the distal end of the humeral plate through the lateral circumference of the proximal forearm may include the steps of making an incision on the proximal posterior of the forearm adjacent to the ulna and inserting the hinge arm through the incision. The step of tunneling the ulnar plate subcutaneously and supramuscularly in the subcutaneous fat layer from the posterior proximal ulna toward the distal end of the ulna may include inserting the ulnar plate through the incision.

The hinge arm and the ulnar plate may be a single preformed unit and the step of tunneling the hinge arm subcutaneously and supramuscularly in the subcutaneous fat layer between the posterior proximal ulna region and the distal end of the humeral plate through the lateral circumference of the proximal forearm; and the step of tunneling the ulnar plate subcutaneously and supramuscularly in the subcutaneous fat layer from the posterior proximal ulna toward the distal end of the ulna may include making an incision an incision on the proximal posterior of the forearm adjacent to the ulna, the length of the incision being the full length of the ulnar plate.

The step of pivotally attaching the hinge arm to the distal end of the humeral plate may include inserting an attachment screw through a hole in the end of the hinge arm adjacent to the humeral plate and through a hole in the distal end of the humeral plate and into the humerus, wherein the attachment screw allows the hinge arm to pivot freely thereon, but locks the humeral plate in the subcutaneous fat layer via locking threads on the attachment screw.

The step of attaching the end of the hinge arm adjacent to the ulnar plate to the proximal end of the ulnar plate may include insertion of an attachment screw through a hole in the end of the hinge arm adjacent to the ulnar plate and through a hole in the proximal end of the ulnar plate and into the ulna. The humeral plate, ulnar plate, hinge arm and attachment screws may be formed from titanium, stainless steel or a bio-compatible polymer material.

BRIEF DESCRIPTION OF THE DRAWINGS

FIG. 1 depicts a prior art external fixation device/technique;

FIG. 2 is depiction of an anterior view of a cross section of an elbow joint in the flexed position and showing an embodiment of the present internal fixation hinge;

FIG. 3 is depiction of a lateral view of a cross section of an elbow joint in the flexed position and showing an embodiment of the present internal fixation hinge;

FIG. 4 is depiction of an anterior view of a cross section of an elbow joint in the extended position and showing an embodiment of the present internal fixation hinge;

FIG. 5 is depiction of a lateral view of a cross section of an elbow joint in the extended position and showing an embodiment of the present internal fixation hinge;

FIG. 7a is a schematic depiction of the manner in which a subcutaneous elongated plate having a contoured end may be placed subcutaneously in the brachium;

FIG. 7b depicts an anterior view of the interior of the brachium with the subcutaneous elongated plate having a contoured end residing in the subcutaneous fat layer above the muscles (supramuscularly) and attached to both ends of the humerus via attachment screws;

FIG. 8a is a schematic depiction of a lateral view of the interior of an elbow joint showing the manner in which a subcutaneous short plate having a contoured end may be placed subcutaneously in the brachium; and FIG. 8b depicts an anterior view of the interior of the elbow joint with the subcutaneous short plate having a contoured end residing in the subcutaneous fat layer above the muscles (supramuscularly) and attached to the distal end of the humerus via attachment screws.

FIG. 18 is depiction of a lateral view of a lower brachium and forearm/hand with a cross section of an elbow joint in the flexed position and showing an embodiment of the present internal elbow fixation hinge.

DETAILED DESCRIPTION OF THE INVENTION

Figures 6A, 6B:
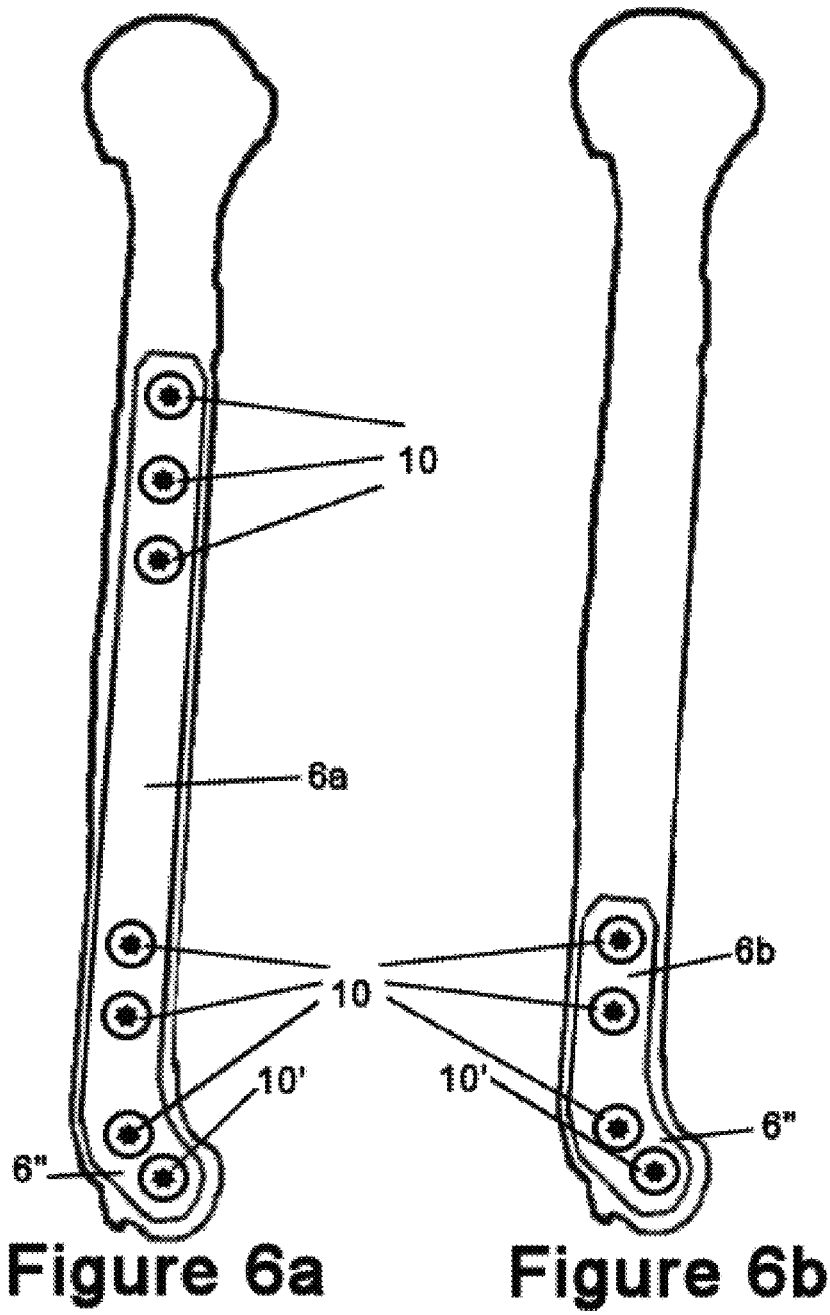
FIG. 6a shows a lateral view of a humerus which has been attached to a subcutaneous elongated plate having a contoured end.
FIG. 6b shows a lateral view of a humerus which has been attached to a subcutaneous short plate having a contoured end.

The instant invention is a novel method and construct for minimally invasive treatment/fixation of an unstable elbow joint (with or without bone fractures) using an internal elbow hinge system with component plates disposed in the subcutaneous fat layer above the muscles.

As mentioned above, the typical prior art external hinged elbow fixator, shown in FIG. 1, has pins screwed 5 into the humerus 2 and the ulna 3 which are connected to bars/clamps 4 and a hinge 30 outside of the skin. FIG. 1 depicts this prior art fixation technique showing how the mechanisms 4 of the external fixator are attached by pins 5 to the humerus 2 and ulna 3 via holes in the skin. The external fixators are cumbersome and can lead to infection. Furthermore, the external fixator does not even address fractures in the humerus or ulna and additional fixation equipment 31 is needed to address these fractures.

Turning now to a detailed description of the present method and device, FIG. 2 is depiction of an anterior view of a cross section of an elbow joint in the flexed position and showing an embodiment of the present internal fixation hinge. The device includes a humeral plate 6 which is attached to the humerus 2 via attachment means 10 and also includes a hinge portion composed of hinge arm 9a and ulnar plate 9b. The ulnar plate 9b is attached to the proximal posterior area of the ulna 3 via attachment means 10. The hinge arm 9a is rotatably attached to the distal end of humeral plate 6 by attachment means 10' and is curved to follow the circumference of the proximal portion of the forearm and remain in the subcutaneous fat layer above the muscle. The hinge arm 9a and the ulnar plate 9b may be formed as a single unit or may be attached to each other by attachment means, welding or other affixation means. As the patient flexes and extends the elbow joint, the hinge 9a arm rotates at the humeral plate 6/hinge arm 9a interface (held together by attachment means 10') in a scissor like fashion. That is the end of the hinge arm 9a adjacent the humeral plate 6 is pivotally connected to the end of the humeral plate 6. This allows the hinge arm 9a and the connected ulna plate 9b to rotate pivotally with respect to humeral plate 6. Thus the combination of plates 6, 9b and hinge arm 9a, along with attachment means 10' forms an elbow hinge that fixates the bones and the joint to allow healing thereof while allowing natural flexion and extension of the joint to minimize any loss of range of motion in the joint during the healing process.

FIG. 3 is depiction of a lateral view of a cross section of an elbow joint in the flexed position and showing an embodiment of the present internal fixation hinge. The device includes a humeral plate 6 which is attached to the humerus 2 via attachment means 10 and also includes a hinge portion composed of hinge arm 9a and ulnar plate 9b attached to the ulna 3 via attachment means 10. The placement of the plates 6, 9b and hinge arm 9a are designed to avoid the necessity of dissecting muscle 1" in installation of the hinge, thereby reducing healing time. As can be seen in FIG. 3, and as stated above the end of the hinge arm 9a adjacent the humeral plate 6 is pivotally connected to the end of the humeral plate 6.

FIG. 4 is depiction of an anterior view of a cross section of an elbow joint in the extended position and showing an embodiment of the present internal fixation hinge. The ulnar plate 9b is attached to the ulna 3 via attachment means 10 and is behind the ulna in this figure. It is apparent in FIG. 4 that the ulnar plate 9b is an integral unit with the hinge arm 9a in this embodiment of the present invention. It can also be seen that humeral plate 6 is affixed to the humerus 2 in a position which is supramuscular.

FIG. 5 is depiction of a lateral view of a cross section of an elbow joint in the extended position and showing an embodiment of the present internal fixation hinge. From the present figure it can be seen how the hinge arm 9a and ulnar plate 9b are pivotally attached to the distal end of the humeral plate 6 and humerus 2. As the elbow flexes and extends, the humeral plate 6 remains in a fixed position attached to the humerus 2 while the hinge arm 9a and ulnar plate 9b pivot as necessary in relation to the humerus 2.

As a first step to installing the elbow hinge of the present invention, the humeral plate 6 may be implanted into the patient. As shown in FIGS. 6a and 6b, the subcutaneous humeral plate 6 may be a long plate 6a (FIG. 6a) or short 6b (FIG. 6b). The chosen length will be based on the fractures (if any) of the humerus. A long plate 6a may be used if there are fractures to the shaft of the humerus 2 and a short plate 6b may be used if there are no fractures to the shaft of the humerus 2. It should be noted that a short plate 6b may be used whether or not there are fractures to the distal end of the humerus 2. Also, the plates 6a, 6b may have a contoured end 6" to conform anatomically with the lateral side of the distal end of the humerus 2". Further, one end of the plate 6a, 6b may have an angled portion 6' designed to be affixed to the lateral epicondyle region in the distal end of the humerus 2.

FIG. 6a shows a lateral view of a humerus which has been attached to a subcutaneous elongated plate 6a having a contoured end 6". FIG. 6b shows a lateral view of a humerus which has been attached to a subcutaneous short plate 6b having a contoured end 6". The subcutaneous elongated plate 6a is used when there is a break in the shaft of the humerus (with or without supracondylar or condylar fractures), while the subcutaneous short plate 6b is used in situations where there are no fractures of the humerus 2 or only supracondylar or condylar fractures (i.e. no fractures of the humeral shaft).

FIG. 7a is a schematic depiction of the manner in which the humeral subcutaneous elongated plate 6a may be placed subcutaneously in the brachium 1'. The subcutaneous elongated plate 6a may be placed into the subcutaneous fat layer through two incisions 8 in the skin. One incision is near the proximal end of the humerus and one is near the distal end of the humerus. The incisions 8 may be approximately 2 inches or less on each end and may preferably be placed in the lateral area of the brachium 1' when the bone segments 2' of the fractured shaft of the humerus are being fixated along with the creation of the elbow hinge. This placement of the elongated plate 6a just under the skin prevents disruption of the muscle tissue and since there is no dissection, there is little chance for infection. Of course, the subcutaneous elongated plate 6a may come in many different sizes to accommodate different bone sizes and may include one or both of the angled end 6' and the contoured end 6". The distal end of long plate the elongated plate 6a may be in contact with distal end of the humerus bone since there is substantially no muscle in this location.

FIG. 7b depicts an anterior view of the interior of the brachium 1' with the subcutaneous elongated plate 6a residing in the subcutaneous fat layer above the muscles 1" (supramuscularly) and attached to both ends of the humerus pieces of the humerus 2' via attachment screws 10. As discussed above, the subcutaneous elongated plate 6a may have one or both of the angled end 6' and the contoured end 6".

FIG. 8a is a schematic depiction of a lateral interior view of an elbow joint. The figure shows the manner in which a subcutaneous short plate 6b may be placed subcutaneously in the brachium 1'. The subcutaneous short plate 6b may be placed into the subcutaneous fat layer through one or two incisions in the skin of the lateral side of the brachium 1' in the vicinity of the distal end of the humerus 2". The subcutaneous short plate 6b may come in different sizes to accommodate different bone sizes and may include one or both of the angled end 6' and the contoured end 6". As with the subcutaneous elongated plate 6a, the subcutaneous short plate 6b is attached to the humerus via attachment screws 10.

FIG. 8b depicts an anterior view of the interior of the elbow joint with the subcutaneous short plate 6b residing in the subcutaneous fat layer above the muscles 1" (supramuscularly) and attached to the distal end of the humerus 2" via attachment screws 10. As discussed above, the subcutaneous short plate 6b may have one or both of the angled end 6' and the contoured end 6". As with subcutaneous elongated plate 6a herein above, the threaded heads of the screws 10 may lock into the threaded holes of the subcutaneous short plate 6b and the shaft of the screws 10 preferably have thread only on the portion thereof which is inserted into the bone. As with the distal end of long plate the elongated plate 6a, the subcutaneous short plate 6b may be in contact with distal end of the humerus bone since there is substantially no muscle in this location.

The holes in the plates 6a, 6b accommodate attachment means to attach the plate to the humerus 2. The holes may be threaded as in locking plate technology. The holes may also be non-threaded and the attachment means may include screws and nuts which can lock the plate near the end of the screws remote from the bone. It should be noted that plates are based on locking plate technology but since they have significantly fewer holes, the device will cost less to produce.

Figure 9:
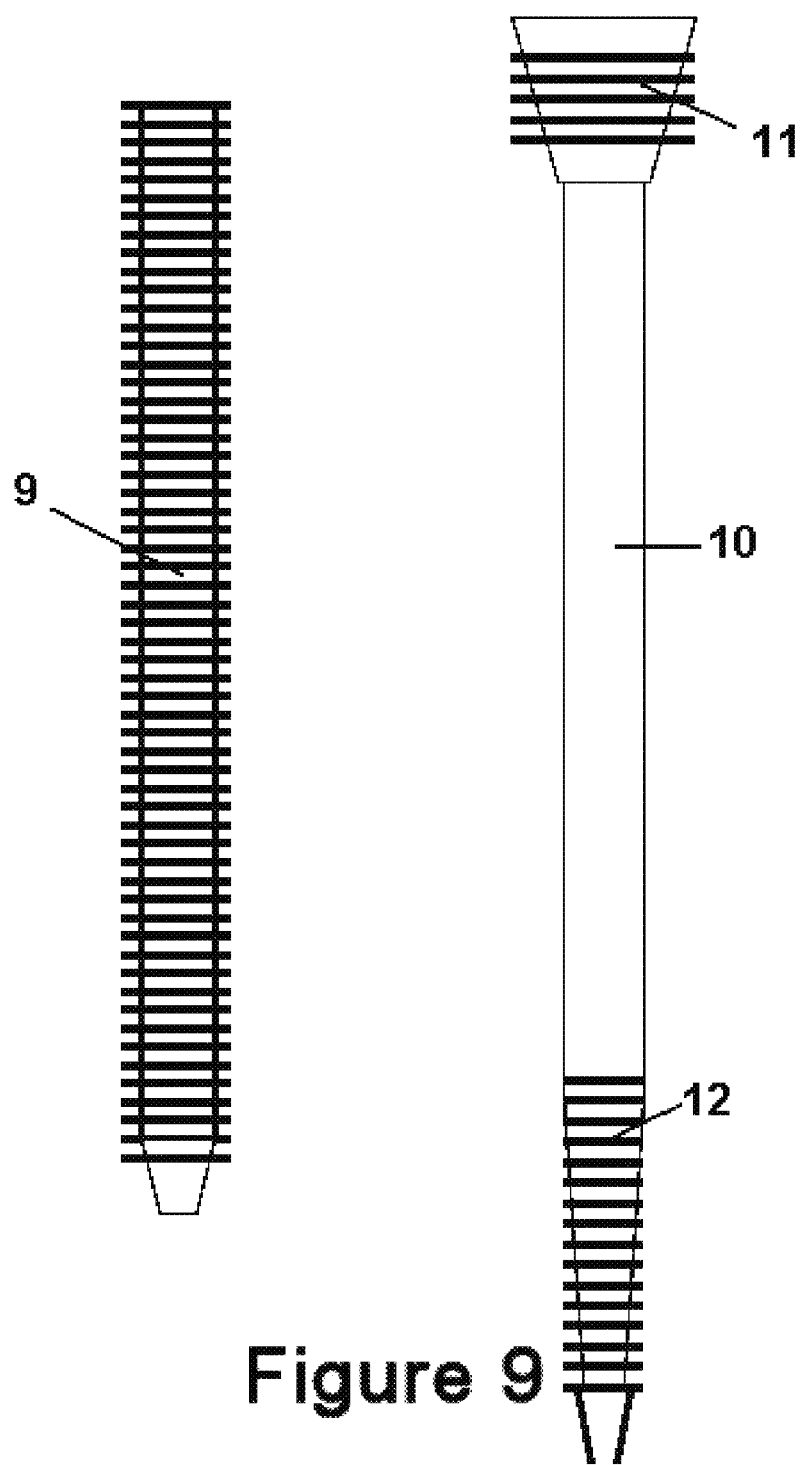
FIG. 9 shows attachment means which may be used in the inventive method and device.

FIG. 9 shows attachment means which may be used in the inventive method and device. Threaded rods 9 may be used to hold the broken bone sections steady as screws 10 are used to attach the device to the bone. Attachment screw 10 preferably has a threaded head 11 to cooperate with the threading in the holes of the elongated plate. Further, the shaft of screw 10 preferably has thread 12 only on the end thereof that will be inserted into the bone. Attachment screws 10 may be cortical screws, such as uni-cortical or bi-cortical screws. Alternatively, threaded rod 9 may be used to steady and attach the plate to the bone using nuts or the like to anchor the plate to the rod in the subcutaneous position, with or without a separate threaded rod 9 for manual manipulation of the bone.

Figure 10:
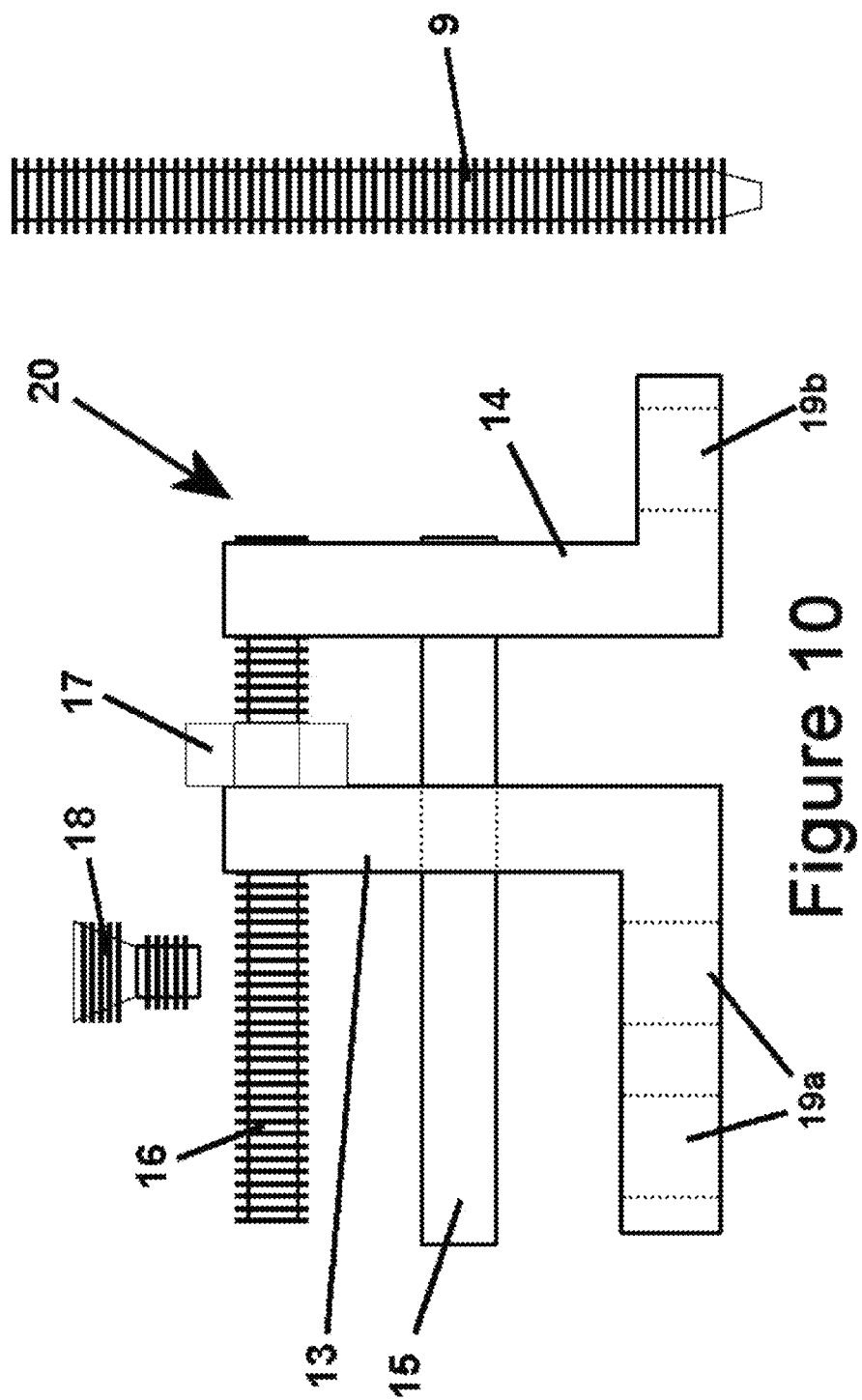
FIG. 10 depicts a preferred distraction device useful in conjunction with the method and device of the present invention.

FIG. 10 depicts a preferred distraction means 20. The distraction means 20 includes two distraction brackets 13 and 14. The distraction brackets 13 and 14 are three dimensional "L" shaped brackets. One of the brackets 13 has one or preferably two holes 19a on the horizontal leg of the "L" and two holes 21a and 21b on the vertical leg of the "L". Holes 19a are used in conjunction with locking screws or bolts 18 to affix bracket 13 to the elongated plate 6 as will be further discussed herein below. Holes 19a may be threaded or not, as needed. Holes 21a and 21b accommodate threaded rod 16 and smooth sliding rod 15, respectively, which rods are attached to bracket 14 as described below. Holes 21a and 21b are preferably not threaded and rods 15 and 16 readily slide through their respective holes.

Bracket 14 includes one hole 19b in the horizontal leg of the "L". Threaded rod 16 and smooth rod 15 are fixedly attached to the vertical leg of the "L" and extend horizontally out from the vertical leg of the "L" toward the through holes 21a and 21b of bracket 13. Hole 19b is used in conjunction with threaded rod 9 to attach bracket 14 to an end of the humerus 2. Finally, treaded rod 16 includes a distraction nut 17 threaded onto rod 16 and positioned between bracket 13 and bracket 14. The distraction nut 17 can push the two brackets 13 and 14 away from each other when the distraction nut 17 is turned the proper direction on the threaded rod 16.

Figure 11:
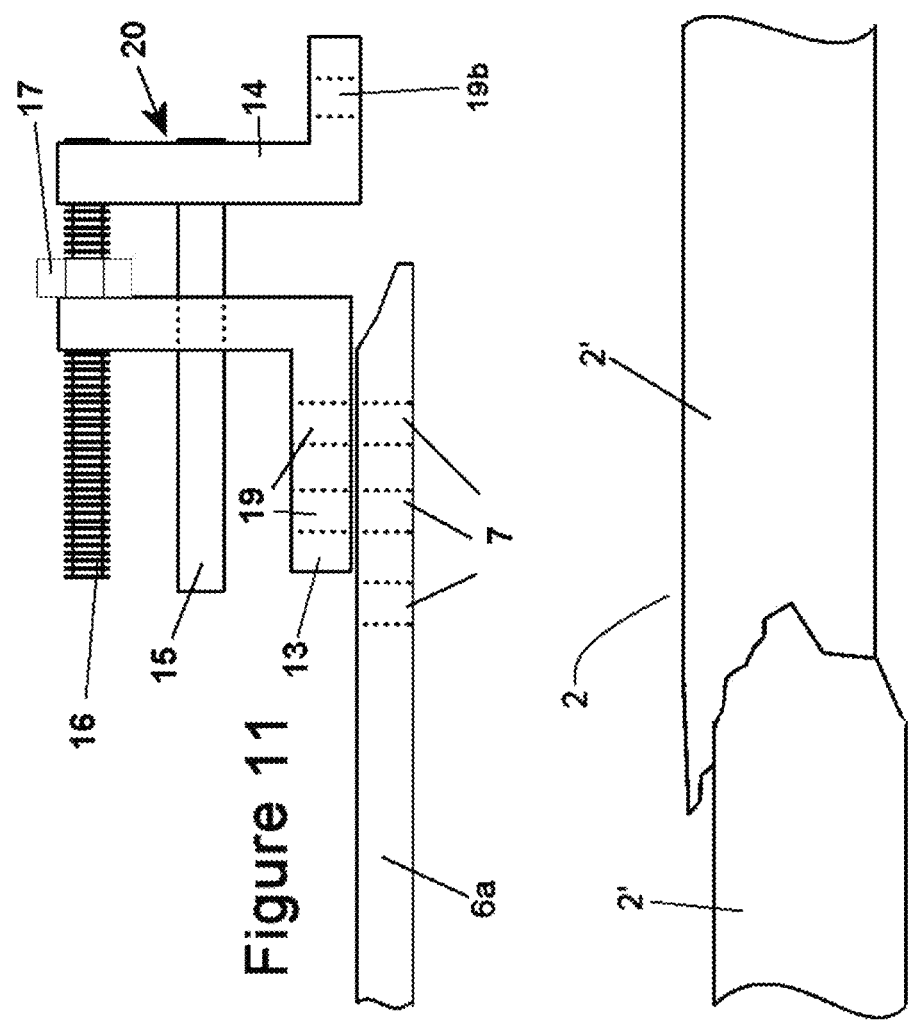
FIG. 11 shows how the distraction device is aligned with the elongated plate for temporary attachment thereto.
Figure 12:
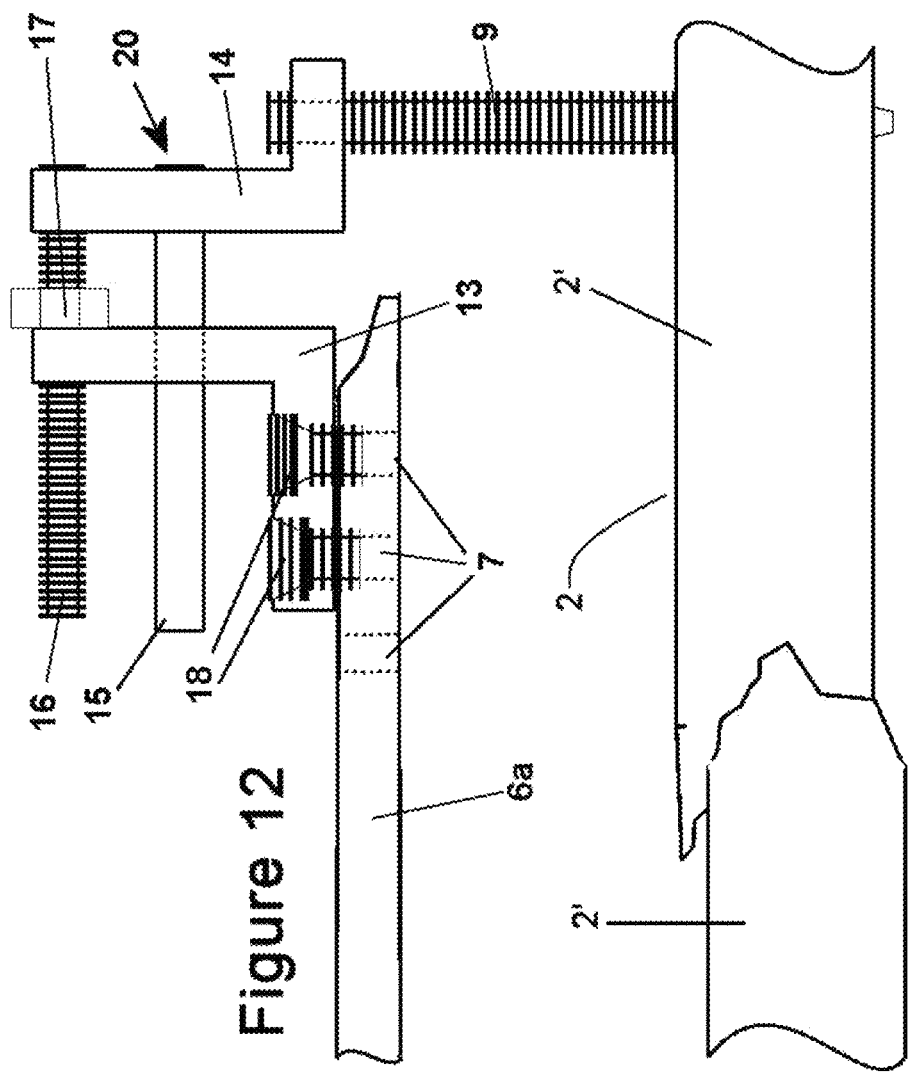
FIG. 12 depicts how the distraction device is attached to the plate using locking screws or bolts.
Figure 13:
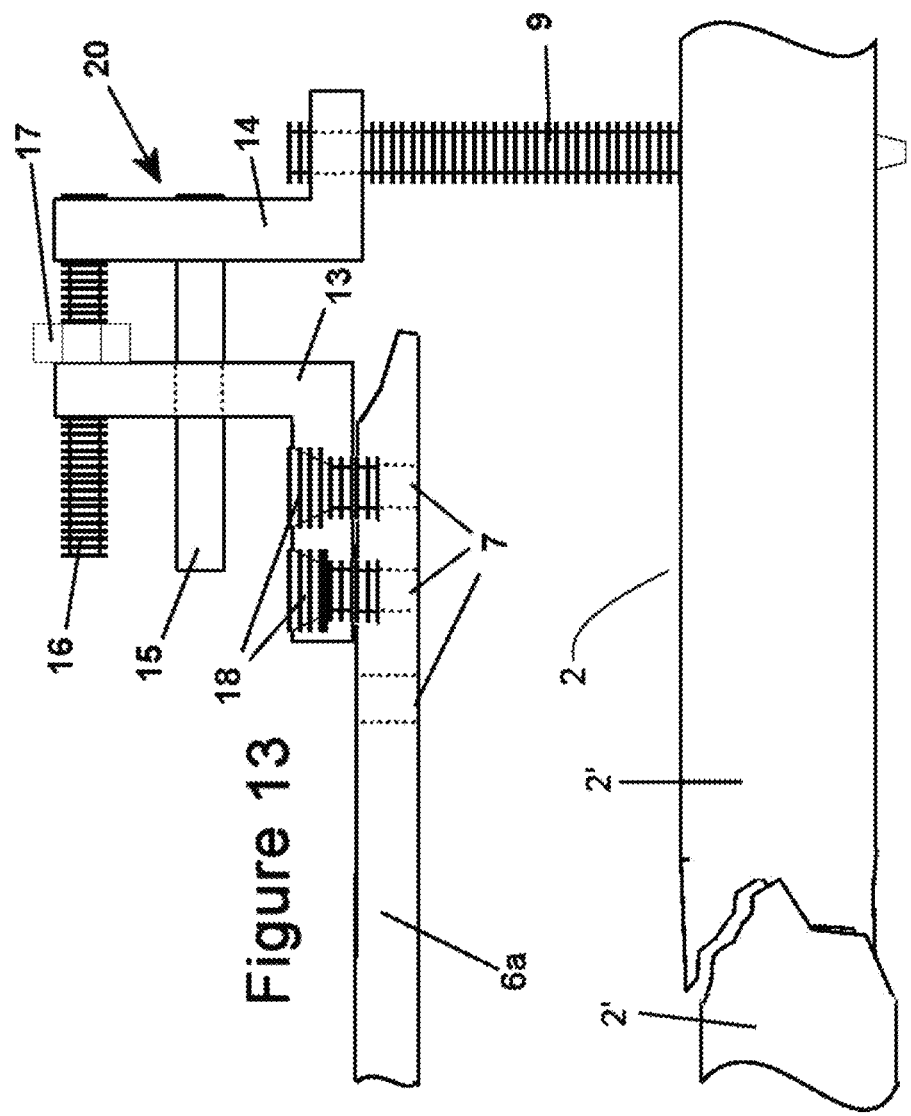
FIG. 13 shows that once the distraction device is attached to both the plate and end of the humerus, the distraction nut is turned to expand distraction device by increasing the distance between the brackets.
Figure 14:
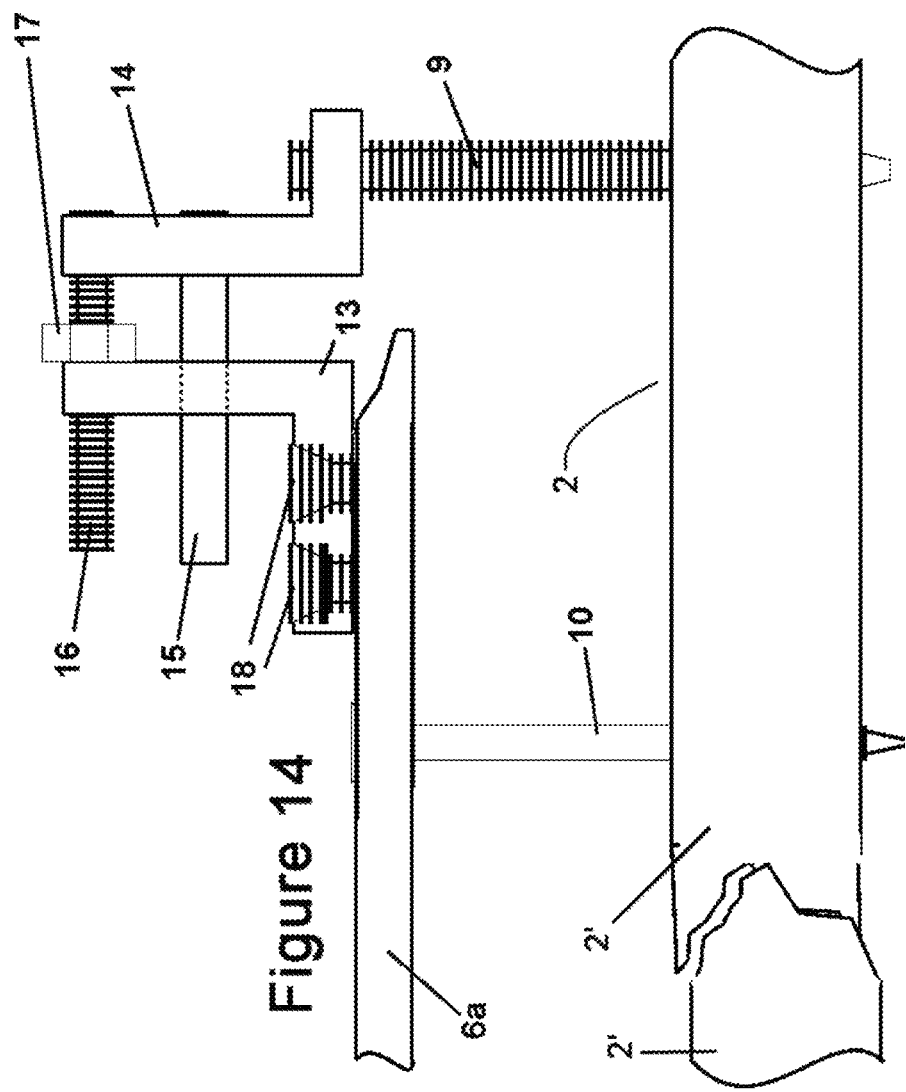
FIG. 14 shows that once the end of the humerus is distracted and aligned, an attachment screw is inserted into the remaining hole on the plate and into the end of the humerus.
Figure 15:
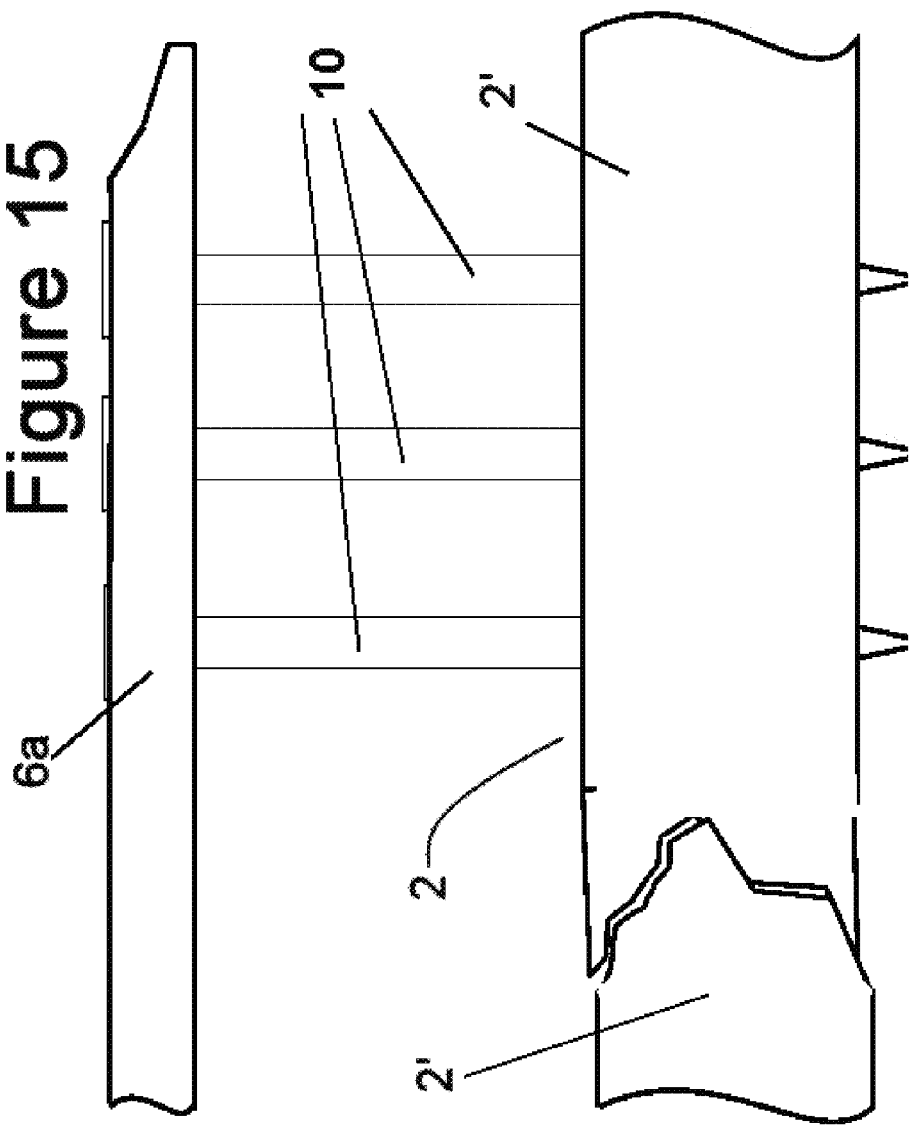
FIG. 15 depicts the removal of the distraction device, and the insertion of the remaining attachment screws through the other holes in the plate and into the end of the humerus.

FIG. 11 shows how the distraction device 20 is aligned with plate 6a. The holes 19a of bracket 13 are aligned with outermost holes 7 of the elongated plate 6a. Once aligned, the distraction device is attached to plate 6a using locking screws or bolts 18 as shown in FIG. 12. The bolts 18 are threaded through holes 19a of bracket 13 and into holes 7 of elongated plate 6a. After the distraction device 20 is attached to plate 6a, a threaded rod is inserted through hole 19b in bracket 14 and into the end of the humerus 2. Once the distraction device 20 is attached to both plate 6a and the end of the humerus 2, then the distraction nut 17 is turned to expand distraction device by increasing the distance between bracket 13 and 14 as shown in FIG. 13. Once the end of the humerus 2 is distracted and aligned, an attachment screw 10 is inserted into the remaining hole 7 on plate 6a and into the end of the humerus 2 as shown in FIG. 14. Once the first attachment screw 10 is in place in the end of the humerus 2, distraction device 20 can be completely removed, and the remaining attachment screws 10 are inserted through the other holes in plate 6a and into the end of the humerus 2 as shown in FIG. 15.

Figure 16:
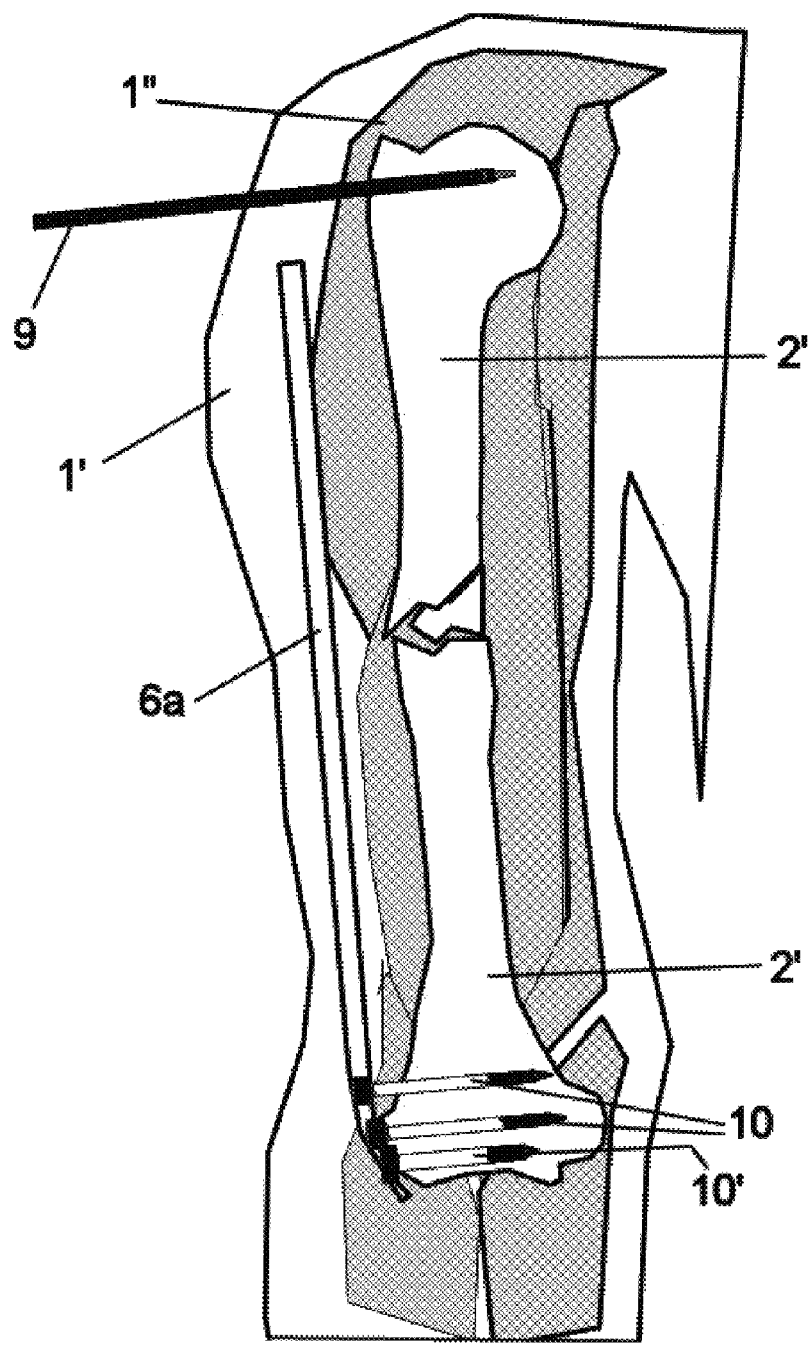
FIG. 16 depicts how a threaded rod may be placed into the proximal end of the humerus after the plate has been placed into the brachium and attached to the distal end of the humerus, the rod being used to distract and align the proximal and distal ends of the humerus.

In another embodiment, once one end of the humerus 2 (preferably the distal end) is attached to the to subcutaneous elongated plate 6a, the other portion of the humerus 2 (preferably the proximal end) must be distracted and aligned to be attached to plate 6a and thereby fixed. FIG. 16 depicts the manner in which the distraction may be performed manually by insertion of a threaded rod 9 into the proximal end 2' of the humerus. This threaded rod 9 is used to manually pull the proximal end of the humerus into place. This is a manual alternative to using the distraction device of FIG. 10.

Figure 17:
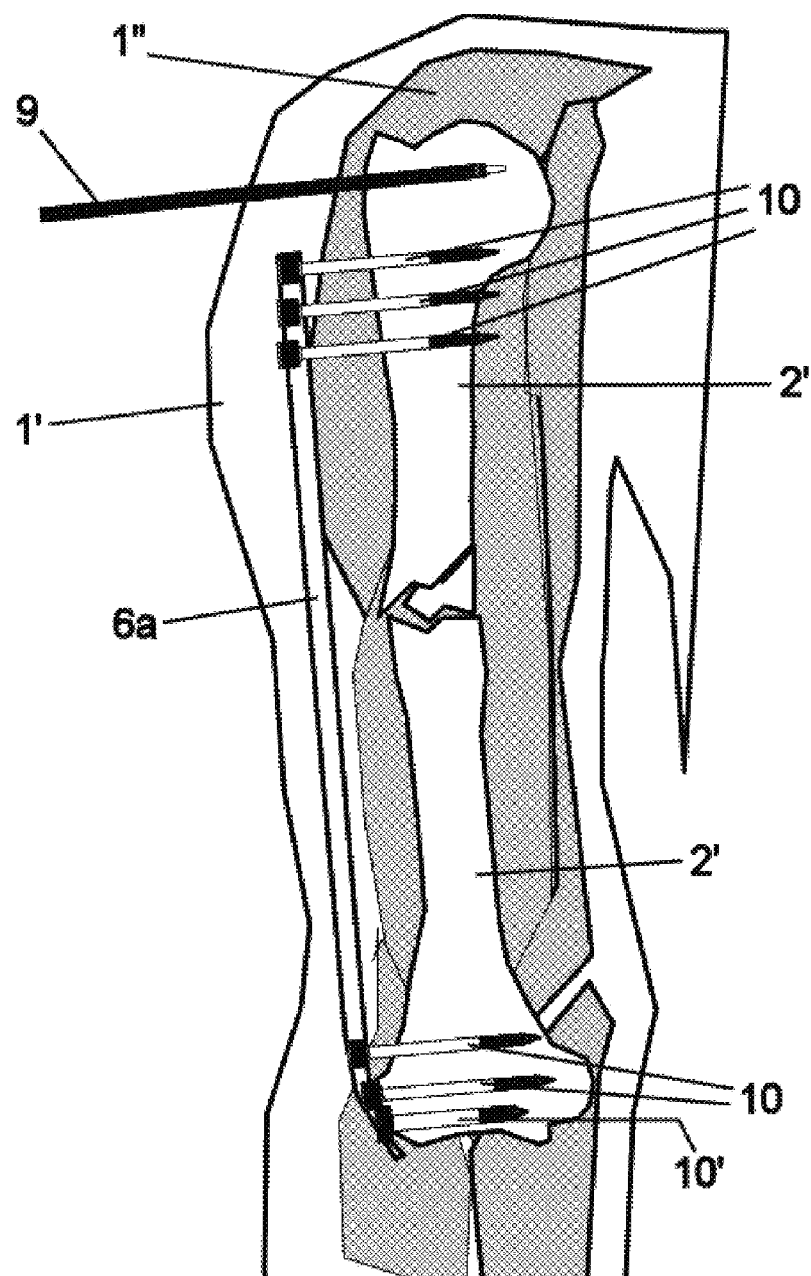
FIG. 17 depicts the insertion of the remaining attachment screws through the other holes in the proximal end of the plate and into the proximal end of the humerus.

Once the proximal end of the humerus 2' is distracted and aligned, attachment screws 10 are inserted into the remaining holes 7 on plate 6a and into the proximal end of the bone 2' as shown in FIG. 17, which depicts the elongated plate 6a attached to both ends of the humerus 2' via attachment screws 10.

After the installation of the humerus plate 6, the hinge arm 9a and the ulnar plate 9b can be subcutaneously inserted. If the hinge arm 9a and the ulnar plate 9b are a single unit, an incision the length of the ulnar plate 9b can be made on the proximal posterior of the forearm adjacent to the ulna. The hinge arm 9a can be subcutaneously tunneled from this incision in an arcing manner around the circumference of the forearm until the end of the hinge arm reaches the distal end of the humeral plate 6, where it can be pivotally attached to the humeral plate 6 and humerus 2. Then once the hinge arm 9a is in place and attached, the ulnar plate 9b may be subcutaneously affixed to the ulna 3. Alternatively, if the hinge arm 9a and the ulnar plate 9b are separate components, a much smaller incision can be made on the proximal posterior of the forearm adjacent to the ulna. The incision can be just large enough to tunnel each of the components through the small incision separately and then attaching the individual components (i.e. the hinge arm 9a and the ulnar plate 9b) to the pivot point and the ulna respectively and then together.

FIG. 18 is depiction of a lateral view of a lower brachium and forearm/hand with a cross section of an elbow joint in the flexed position and showing an embodiment of the present internal fixation hinge. FIG. 18 shows the final hinge installed in an elbow. The hinge arm 9a pivots with respect to the humerus plate 6b on attachment means 10'. The ulnar plate 9b is attached to hinge arm 9a and pivots with the arm when the elbow joint flexes and extends. The hinge arm 9a pivots freely on attachment means 10' while attachment means 10' may lock into the hole in humeral plate 6b. Obviously, the longer humeral plate 6a may be substituted as needed for the short plate 6b.

The humeral plates, ulnar plates, hinge arm and attachment means/screws of the present invention may be formed from titanium, stainless steel or a bio-compatible polymer material. It is to be expected that considerable variations may be made in the embodiments disclosed herein without departing from the spirit and scope of this invention. Accordingly, the significant improvements offered by this invention are to be limited only by the scope of the following claims.

The invention claimed is:

1. A surgical method for minimally invasive treatment of an unstable elbow comprising the steps of:
surgically installing an internal elbow hinge, said elbow hinges including a humeral plate, and ulnar plate, and a hinge arm pivotally connected to said humeral plate and fixedly connected to said ulnar plate;
wherein said step of installing said internal elbow hinge comprises the steps of:
tunneling said humeral plate subcutaneously and supramuscularly in the subcutaneous fat layer adjacent the humerus, the length dimension of said humeral plate being generally substantially parallel to the length dimension of said humerus;
attaching said humeral plate to said humerus, said humeral plate spanning at least the distal region of said humerus, wherein said humeral plate remains disposed in the subcutaneous fat layer and away from, but substantially parallel to said humerus once attached to said humerus;
tunneling said hinge arm subcutaneously and supramuscularly in the subcutaneous fat layer between the posterior proximal ulna region and the distal end of said humeral plate through the lateral circumference of the proximal forearm;
pivotally attaching said hinge arm to said distal end of said humeral plate;
tunneling said ulnar plate subcutaneously and supramuscularly in the subcutaneous fat layer from the posterior proximal ulna toward the distal end of said ulna, the length dimension of said ulnar plate being generally substantially parallel to the length dimension of said ulna;
attaching said ulnar plate to said ulna, said ulnar plate spanning at least the proximal region of said ulna, wherein said ulnar plate remains disposed in the subcutaneous fat layer and away from, but substantially parallel to said ulna once attached to said ulna; and
attaching the end of said hinge arm adjacent to said ulnar plate to the proximal end of said ulnar plate.

2. The surgical method of claim 1, wherein said step of attaching said humeral plate to said humerus includes attaching said humeral plate to said humerus by inserting attachment screws through holes in said humeral plate and into said humerus; and
said step of attaching said ulnar plate to said ulna includes attaching said ulnar plate to said ulna by inserting attachment screws through holes in said ulnar plate and into said ulna.

3. The surgical method of claim 2, wherein said holes in said humeral and ulnar plates are threaded and said attachment screws have threaded heads and said threaded heads allow said attachment screws to lock into said threaded holes of said humeral and ulnar plates.

4. The surgical method of claim 1, wherein said humeral plate has an angled and/or contoured distal end to anatomically match the lateral epicondyle region of the distal end of said humerus.

5. The surgical method of claim 4, wherein said humeral plate, ulnar plate, hinge arm and attachment screws are formed from titanium, stainless steel or a bio-compatible polymer material.

6. The surgical method of claim 1, wherein said humeral plate is an elongated humeral plate that spans substantially the length of said humerus and said tunneling step includes creating one or more incisions in the skin on the lateral part of the brachium through which said elongated humeral plate can be inserted into the subcutaneous fat layer.

7. The surgical method of claim 6, wherein said step of attaching said humeral plate to said humerus further includes inserting attachment means through holes in the proximal end of said elongated humeral plate and the step distracting and aligning a humerus having a fracture of the humeral shaft.

8. The surgical method of claim 7, wherein said step of distracting and aligning said humerus having a fracture of the humeral shaft includes inserting a threaded rod into the proximal end of said humerus having a fracture of the humeral shaft and manually distracting and aligning said humerus having a fracture of the humeral shaft.

9. The surgical method of claim 8, wherein said step of distracting and aligning said humerus having a fracture of the humeral shaft includes using a distraction device.

10. The surgical method of claim 9, wherein said step of using a distraction device includes the step of attaching said distraction device to holes in the proximal end of elongated humeral plate and also attaching said distraction device to the proximal end of said humerus having a fracture of the humeral shaft.

11. The surgical method of claim 10, wherein said distraction device has two brackets, where the first of said brackets is attached to said holes in the proximal end of said elongated plate and the second of said brackets is attached to said proximal end of said humerus having a fracture of the humeral shaft.

12. The surgical method of claim 11, wherein said distraction device further includes an expansion device which is attached to both brackets and includes a threaded rod and a nut which is threaded onto said threaded rod, wherein said nut pushes against one of said brackets causing said brackets to expand away from each other thereby providing for distraction of said humerus having a fracture of the humeral shaft.

13. The surgical method of claim 12, wherein said step of attaching said humeral plate to said humerus further includes the step of inserting an attachment screw through a hole in a proximal end of said elongated humeral plate into the proximal end of said humerus having a fracture of the humeral shaft once said step of distracting and aligning said humerus having a fracture of the humeral shaft is completed; and
includes the step of removing said distraction device after said step of inserting an attachment screw through a hole in the proximal end of said elongated humeral plate into the proximal end of said humerus having a fracture of the humeral shaft.

14. The surgical method of claim 13, wherein said step of attaching said humeral plate to said humerus further includes the step of inserting an additional attachment screw through each of the remaining holes in the proximal end of said elongated plate into the proximal end of said humerus.

15. The surgical method of claim 1, wherein said step of tunneling said hinge arm subcutaneously and supramuscularly in the subcutaneous fat layer between the posterior proximal ulna region and the distal end of said humeral plate through the lateral circumference of the proximal forearm includes the steps of making an incision on the proximal posterior of the forearm adjacent to said ulna and inserting said hinge arm through said incision.

16. The surgical method of claim 15, wherein said step of tunneling said ulnar plate subcutaneously and supramuscularly in the subcutaneous fat layer from the posterior proximal ulna toward the distal end of said ulna includes inserting said ulnar plate through said incision.

17. The surgical method of claim 1, wherein said hinge arm and said ulnar plate are a single preformed unit.

18. The surgical method of claim 17, wherein said step of tunneling said hinge arm subcutaneously and supramuscularly in the subcutaneous fat layer between the posterior proximal ulna region and the distal end of said humeral plate through the lateral circumference of the proximal forearm and said step of tunneling said ulnar plate subcutaneously and supramuscularly in the subcutaneous fat layer from the posterior proximal ulna toward the distal end of said ulna includes making an incision an incision on the proximal posterior of the forearm adjacent to said ulna, the length of said incision being the full length of said ulnar plate.

19. The surgical method of claim 1, wherein said step of pivotally attaching said hinge arm to said distal end of said humeral plate includes inserting an attachment screw through a hole in the end of said hinge arm adjacent to said humeral plate and through a hole in the distal end of said humeral plate and into said humerus, said attachment screw allowing said hinge arm to pivot freely thereon, but locking said humeral plate in the subcutaneous fat layer via locking threads on said attachment screw.

20. The surgical method of claim 1, wherein said step of attaching said end of said hinge arm adjacent to said ulnar plate to said proximal end of said ulnar plate includes insertion of an attachment screw through a hole in said end of said hinge arm adjacent to said ulnar plate and through a hole in said proximal end of said ulnar plate and into said ulna.

* * * * *